US008540628B2

(12) United States Patent  (10) Patent No.: US 8,540,628 B2
O'Prey et al.  (45) Date of Patent: Sep. 24, 2013

(54) EXPANDABLE THORACIC ACCESS PORT

(75) Inventors: Cormac O'Prey, Bishops Stortford (GB); Simon Roderick Grover, Cambridge (GB); Charlotte Adele Clark, Cambridge (GB); Valerie Anne Scott, Cambridge (GB)

(73) Assignee: Covidien LP, Mansfield, MA (US)

( * ) Notice: Subject to any disclaimer, the term of this patent is extended or adjusted under 35 U.S.C. 154(b) by 175 days.

(21) Appl. No.: 13/005,626

(22) Filed: Jan. 13, 2011

(65) Prior Publication Data

US 2011/0201893 A1 Aug. 18, 2011

Related U.S. Application Data

(60) Provisional application No. 61/304,153, filed on Feb. 12, 2010.

(51) Int. Cl.
*A61B 1/32* (2006.01)
(52) U.S. Cl.
USPC .......................................... 600/208
(58) Field of Classification Search
USPC ................ 600/201–210, 216, 217, 224, 228, 600/229, 231, 233; 604/164.03; 606/108
See application file for complete search history.

(56) References Cited

U.S. PATENT DOCUMENTS

| 1,780,912 | A | 11/1930 | Gau |
| 1,810,466 | A | 6/1931 | Deutsch |
| 2,313,164 | A | 3/1943 | Nelson |
| 2,541,516 | A | 2/1951 | Ivory et al. |
| 2,812,758 | A | 11/1957 | Blumenschein |
| 3,782,370 | A | 1/1974 | McDonald |
| 3,807,393 | A | 4/1974 | McDonald |
| 3,965,890 | A | 6/1976 | Gauthier |
| 4,130,113 | A | 12/1978 | Graham |
| 4,263,899 | A | 4/1981 | Burgin |
| 4,553,537 | A | 11/1985 | Rosenberg |
| 5,007,900 | A | 4/1991 | Picha et al. |
| 5,052,374 | A | 10/1991 | Alvarez-Jacinto |
| 5,080,088 | A | 1/1992 | LeVahn |
| 5,125,396 | A | 6/1992 | Ray |
| 5,169,387 | A | 12/1992 | Kronner |
| 5,231,974 | A | 8/1993 | Giglio et al. |

(Continued)

FOREIGN PATENT DOCUMENTS

| DE | 10001695 | 2/2001 |
| DE | 102009014527 | 9/2010 |

(Continued)

OTHER PUBLICATIONS

EP Search Report 11 25 0163 dated Jun. 7, 2011.

(Continued)

*Primary Examiner* — Nicholas Woodall

(57) ABSTRACT

A surgical access assembly includes a body having first and second side panels opposing one another and first and second end panels interconnecting the side panels. The first and second end panels are moveable between a folded position and an expanded position to correspondingly move the first and second side panels with respect to one another between an approximated position and a spaced apart position. In the spaced apart position, the first and second side panels are flexed outwardly and apart from one another to define a passageway therebetween. A flexible membrane is coupled to the first and second side panels and extends proximally therefrom.

9 Claims, 10 Drawing Sheets

(56) References Cited

U.S. PATENT DOCUMENTS

| | | |
|---|---|---|
| 5,232,451 A | 8/1993 | Freitas et al. |
| 5,269,754 A | 12/1993 | Rydell |
| 5,279,575 A | 1/1994 | Sugarbaker |
| 5,330,501 A | 7/1994 | Tovey et al. |
| 5,346,484 A | 9/1994 | Van Lindert |
| 5,391,156 A | 2/1995 | Hildwein et al. |
| 5,437,683 A | 8/1995 | Neumann et al. |
| 5,445,615 A | 8/1995 | Yoon |
| 5,460,170 A | 10/1995 | Hammerslag |
| 5,480,410 A | 1/1996 | Cuschieri |
| 5,490,843 A | 2/1996 | Hildwein et al. |
| 5,503,617 A | 4/1996 | Jako |
| 5,520,610 A | 5/1996 | Giglio et al. |
| 5,524,644 A | 6/1996 | Crook |
| 5,556,385 A | 9/1996 | Andersen |
| 5,562,677 A | 10/1996 | Hildwein et al. |
| 5,653,705 A | 8/1997 | De la Torre et al. |
| 5,697,891 A | 12/1997 | Hori |
| 5,728,103 A | 3/1998 | Picha et al. |
| 5,755,660 A | 5/1998 | Tyagi |
| 5,755,661 A | 5/1998 | Schwartzman |
| 5,772,583 A | 6/1998 | Wright et al. |
| 5,776,110 A | 7/1998 | Guy et al. |
| 5,779,629 A | 7/1998 | Hohlen |
| 5,788,630 A | 8/1998 | Furnish |
| 5,803,921 A | 9/1998 | Bonadio |
| 5,810,721 A | 9/1998 | Mueller et al. |
| 5,846,193 A | 12/1998 | Wright |
| 5,875,782 A | 3/1999 | Ferrari et al. |
| 5,879,291 A | 3/1999 | Kolata et al. |
| 5,906,577 A | 5/1999 | Beane et al. |
| 5,908,382 A | 6/1999 | Koros et al. |
| 5,931,778 A | 8/1999 | Furnish |
| 5,935,107 A | 8/1999 | Taylor et al. |
| 5,944,736 A | 8/1999 | Taylor et al. |
| 5,951,466 A | 9/1999 | Segermark et al. |
| 5,951,467 A | 9/1999 | Picha et al. |
| 5,957,835 A | 9/1999 | Anderson et al. |
| 5,967,972 A | 10/1999 | Santilli et al. |
| 5,993,385 A | 11/1999 | Johnston et al. |
| 6,024,736 A | 2/2000 | De la Torre et al. |
| 6,033,362 A | 3/2000 | Cohn |
| 6,033,425 A | 3/2000 | Looney et al. |
| 6,036,641 A | 3/2000 | Taylor et al. |
| 6,048,309 A | 4/2000 | Flom et al. |
| 6,074,380 A | 6/2000 | Byrne et al. |
| 6,113,535 A | 9/2000 | Fox et al. |
| 6,120,436 A | 9/2000 | Anderson et al. |
| 6,132,370 A | 10/2000 | Furnish et al. |
| 6,142,935 A | 11/2000 | Flom et al. |
| 6,159,231 A | 12/2000 | Looney et al. |
| 6,162,172 A | 12/2000 | Cosgrove et al. |
| 6,231,506 B1 | 5/2001 | Hu et al. |
| 6,254,533 B1 | 7/2001 | Fadem et al. |
| 6,254,534 B1 | 7/2001 | Butler et al. |
| 6,283,912 B1 | 9/2001 | Hu et al. |
| 6,309,349 B1 | 10/2001 | Bertolero et al. |
| 6,312,377 B1 | 11/2001 | Segermark et al. |
| 6,331,158 B1 | 12/2001 | Hu et al. |
| 6,332,468 B1 | 12/2001 | Benetti |
| 6,354,995 B1 | 3/2002 | Hoftman et al. |
| 6,361,492 B1 | 3/2002 | Santilli |
| 6,382,211 B1 | 5/2002 | Crook |
| 6,443,957 B1 | 9/2002 | Addis |
| 6,450,983 B1 | 9/2002 | Rambo |
| 6,458,079 B1 | 10/2002 | Cohn et al. |
| 6,500,116 B1 | 12/2002 | Knapp |
| 6,517,563 B1 | 2/2003 | Paolitto et al. |
| 6,547,725 B1 | 4/2003 | Paolitto et al. |
| 6,585,442 B2 | 7/2003 | Brei et al. |
| 6,599,240 B2 | 7/2003 | Puchovsky et al. |
| 6,599,292 B1 | 7/2003 | Ray |
| 6,616,605 B2 | 9/2003 | Wright et al. |
| 6,652,454 B2 | 11/2003 | Hu et al. |
| 6,723,044 B2 | 4/2004 | Pulford et al. |
| 6,730,021 B2 | 5/2004 | Vassiliades, Jr. et al. |
| 6,730,022 B2 | 5/2004 | Martin et al. |
| 6,746,396 B1 | 6/2004 | Segermark et al. |
| 6,746,467 B1 | 6/2004 | Taylor et al. |
| 6,814,078 B2 | 11/2004 | Crook |
| 6,814,700 B1 | 11/2004 | Mueller et al. |
| 6,840,951 B2 | 1/2005 | De la Torre et al. |
| 6,846,287 B2 | 1/2005 | Bonadio et al. |
| 6,958,037 B2 | 10/2005 | Ewers et al. |
| 7,033,319 B2 | 4/2006 | Pulford et al. |
| 7,052,454 B2 | 5/2006 | Taylor |
| 7,144,368 B2 | 12/2006 | Larson et al. |
| 7,147,599 B2 | 12/2006 | Phillips et al. |
| 7,179,225 B2 | 2/2007 | Shluzas et al. |
| 7,195,592 B2 | 3/2007 | Ravikumar et al. |
| 7,220,228 B2 | 5/2007 | Hu et al. |
| 7,226,451 B2 | 6/2007 | Shluzas et al. |
| 7,229,408 B2 | 6/2007 | Douglas et al. |
| 7,238,154 B2 | 7/2007 | Ewers et al. |
| 7,261,688 B2 | 8/2007 | Smith et al. |
| 7,270,632 B2 | 9/2007 | Santilli |
| 7,300,399 B2 | 11/2007 | Bonadio et al. |
| 7,344,495 B2 | 3/2008 | Ravikumar et al. |
| 7,387,126 B2 | 6/2008 | Cox et al. |
| 7,393,322 B2 | 7/2008 | Wenchell |
| 7,507,202 B2 | 3/2009 | Schoellhorn |
| 7,507,235 B2 | 3/2009 | Keogh et al. |
| 7,537,564 B2 | 5/2009 | Bonadio et al. |
| 7,540,839 B2 | 6/2009 | Butler et al. |
| 7,559,893 B2 | 7/2009 | Bonadio et al. |
| 7,566,302 B2 | 7/2009 | Schwer |
| 7,585,277 B2 | 9/2009 | Taylor et al. |
| 7,594,888 B2 | 9/2009 | Raymond et al. |
| 7,650,887 B2 | 1/2010 | Nguyen et al. |
| 2001/0002429 A1 | 5/2001 | Hu et al. |
| 2001/0020121 A1 | 9/2001 | Hu et al. |
| 2001/0041827 A1 | 11/2001 | Spence et al. |
| 2002/0004628 A1 | 1/2002 | Hu et al. |
| 2002/0095139 A1 | 7/2002 | Keogh et al. |
| 2002/0099269 A1 | 7/2002 | Martin et al. |
| 2002/0099271 A1 | 7/2002 | Knapp |
| 2002/0137989 A1 | 9/2002 | Clem et al. |
| 2003/0191371 A1 | 10/2003 | Smith et al. |
| 2004/0049099 A1* | 3/2004 | Ewers et al. .................. 600/206 |
| 2004/0054353 A1 | 3/2004 | Taylor |
| 2004/0059192 A1 | 3/2004 | Cartier et al. |
| 2004/0225195 A1 | 11/2004 | Spence et al. |
| 2005/0096508 A1 | 5/2005 | Valentini et al. |
| 2005/0171403 A1 | 8/2005 | Paolitto et al. |
| 2005/0228232 A1 | 10/2005 | Gillinov et al. |
| 2005/0267336 A1 | 12/2005 | Bertolero et al. |
| 2005/0283050 A1 | 12/2005 | Gundlapalli et al. |
| 2006/0004261 A1 | 1/2006 | Douglas |
| 2006/0089537 A1 | 4/2006 | Schoellhorn |
| 2006/0106416 A1 | 5/2006 | Raymond et al. |
| 2006/0129165 A1* | 6/2006 | Edoga et al. .................. 606/108 |
| 2006/0149137 A1 | 7/2006 | Pingleton et al. |
| 2006/0149306 A1 | 7/2006 | Hart et al. |
| 2006/0155170 A1 | 7/2006 | Hanson et al. |
| 2007/0027364 A1 | 2/2007 | Schwer |
| 2007/0073110 A1 | 3/2007 | Larson et al. |
| 2008/0132766 A1 | 6/2008 | Dant et al. |
| 2008/0234550 A1 | 9/2008 | Hawkes et al. |
| 2009/0204067 A1 | 8/2009 | Abu-Halawa |
| 2009/0265941 A1 | 10/2009 | Kurrus |
| 2009/0299148 A1 | 12/2009 | White et al. |
| 2010/0210916 A1 | 8/2010 | Hu et al. |
| 2010/0234689 A1 | 9/2010 | Wagner et al. |
| 2010/0261970 A1 | 10/2010 | Shelton, IV et al. |

FOREIGN PATENT DOCUMENTS

| | | |
|---|---|---|
| EP | 0177177 | 4/1986 |
| EP | 2179699 | 4/2010 |
| EP | 2 228 014 | 9/2010 |
| EP | 2 228 024 | 9/2010 |
| EP | 2 238 931 A1 | 10/2010 |
| EP | 2 417 922 | 2/2012 |
| GB | 2275420 | 8/1994 |
| WO | WO95/00197 | 1/1995 |

| | | |
|---|---|---|
| WO | WO95/15715 | 6/1995 |
| WO | WO 01/08563 A2 | 2/2001 |
| WO | WO-03/034908 | 5/2003 |
| WO | WO-2005/089655 | 9/2005 |
| WO | WO 2010/136805 | 12/2010 |
| WO | WO 2011/079374 | 7/2011 |

OTHER PUBLICATIONS

EP Search Report 11 25 0164 dated Jun. 8, 2011.
EP Search Report EP 12160423.5 dated Jun. 25, 2012.

* cited by examiner

EXPANDABLE THORACIC ACCESS PORT

This application claims priority from provisional application Ser. No. 61/304,153, filed Feb. 12, 2010, the entire contents of which are incorporated herein by reference.

BACKGROUND

1. Technical Field

The present disclosure relates generally to devices and techniques for performing surgical procedures. More particularly, the present disclosure relates to an access device for minimally invasive surgery.

2. Background of the Related Art

In an effort to reduce trauma and recovery time, many surgical procedures are performed through small openings in the skin, such as an incision or a natural body orifice. For example, these procedures include laparoscopic procedures, which are generally performed within the confines of a patient's abdomen, and thoracic procedures, which are generally performed within a patient's chest cavity.

Specific surgical instruments have been developed for use during such minimally invasive surgical procedures. These surgical instruments typically include an elongated shaft with operative structure positioned at a distal end thereof, such as graspers, clip appliers, specimen retrieval bags, etc.

During minimally invasive procedures, the clinician creates an opening in the patient's body wall, oftentimes by using an obturator or trocar, and thereafter positions an access assembly within the opening. The access assembly includes a passageway extending therethrough to receive one or more of the above-mentioned surgical instruments for positioning within the internal work site, e.g. the body cavity.

During minimally invasive thoracic procedures, an access assembly is generally inserted into a space located between the patient's adjacent ribs that is known as the intercostal space, and then surgical instruments can be inserted into the internal work site through the passageway in the access assembly.

In the interests of facilitating visualization, the introduction of certain surgical instruments, and/or the removal of tissue specimens during minimally invasive thoracic procedures, it may be desirable to spread tissue adjacent the ribs defining the intercostal space. Additionally, during these procedures, firm, reliable placement of the access assembly is desirable to allow the access assembly to withstand forces that are applied during manipulation of the instrument(s) inserted therethrough. However, reducing patient trauma during the procedure, discomfort during recovery, and the overall recovery time remain issues of importance. Thus, there exists a need for thoracic access ports which minimize post operative patient pain while enabling atraumatic retraction of tissue and which do not restrict access to the body cavity, as will as facilitates removal of tissue specimens from the body cavity.

SUMMARY

In accordance with one aspect of the present disclosure, a surgical access assembly, or access port, for positioning within an opening in tissue is provided. In one aspect, the surgical access assembly includes a body having first and second side panels and first and second end panels. The first and second side panels oppose one another and are interconnected by the first and second end panels. The first and second end panels are moveable between a folded position and an expanded position. When the end panels are disposed in the folded position, the side panels are in an approximated position with respect to one another and preferably each side panel defines a concave inner surface. When the end panels are moved to the extended position, the first and second side panels are flexed outwardly and apart from one another such that each side panel preferably defines a convex inner surface and such that a passageway is defined between the side panels. A flexible membrane is coupled to the first and second body members and extends proximally therefrom.

In one embodiment, the flexible membrane is coupled to a ring at a proximal end thereof and the ring is configured to maintain the flexible membrane in an open configuration. Further, the ring, in some embodiments, may be configured to rotate, or roll with respect to the flexible membrane for selectively tensioning the flexible membrane.

In some embodiments, one or more ribbons are coupled to the end panels for manipulating the positioning of the end panels, i.e., to move the end panels between the folded position and the expanded position.

Cushioning may be disposed on the outwardly facing surfaces of the side panels to protect surrounding tissue when the access assembly is disposed through an opening in tissue. Further, reinforcement strips may be disposed within each of the side panels to help define the shape of the side panels in each of the approximated and spaced apart positions.

In some embodiments, the end panels are biased toward the expanded position. The side panels may be bistable, i.e., the side panels may be retainable in both the approximated position and the spaced apart position.

In accordance with another aspect of the present disclosure, a surgical access assembly for positioning within an opening in tissue is provided comprising a body composed of substantially rigid material and having an opening dimensioned and configured to receive surgical instruments therethrough. A plurality of flexible members extend distally in a first direction and an elastic membrane extends proximally from the body in a second direction. An outer tensioning member connected to the elastic membrane is movable to tension the elastic membrane to retract soft tissue adjacent the tissue opening.

In one embodiment, the membrane is coupled to the tensioning member at a proximal end thereof. In one embodiment, the tensioning member comprises a ring configured to rotate about a circumference thereof to roll the membrane therearound for selectively tensioning the membrane. The assembly can include at least one ribbon. In one embodiment, the flexible members are biased toward the expanded position.

A method of accessing an internal cavity of a patient is also provided in accordance with another aspect of the present disclosure. The method includes forming an opening in the patient's tissue and providing an access assembly with first and second side panels and first and second end panels. Next, with the end panels in the folded position, the access assembly is inserted through the opening in the patient's tissue such that the body of the access assembly is positioned within an intercostal space defined between adjacent ribs of the patient and such that the flexible membrane extends proximally from the opening in tissue. The end panels are then moved to the expanded position such that the side panels are moved from the approximated position to the spaced apart position to expand the intercostal space and to define a passageway port into the patient's internal body cavity.

The method may further include introducing surgical instrumentation and a tissue specimen through the access assembly.

The method can further include moving the end panels back to the folded position to move the side panels from the spaced apart position to the approximated position. The access assembly can then be removed from the opening in tissue.

BRIEF DESCRIPTION OF THE DRAWINGS

Various embodiments of the subject access port are described herein with reference to the drawings wherein.

DETAILED DESCRIPTION

Figure 1:
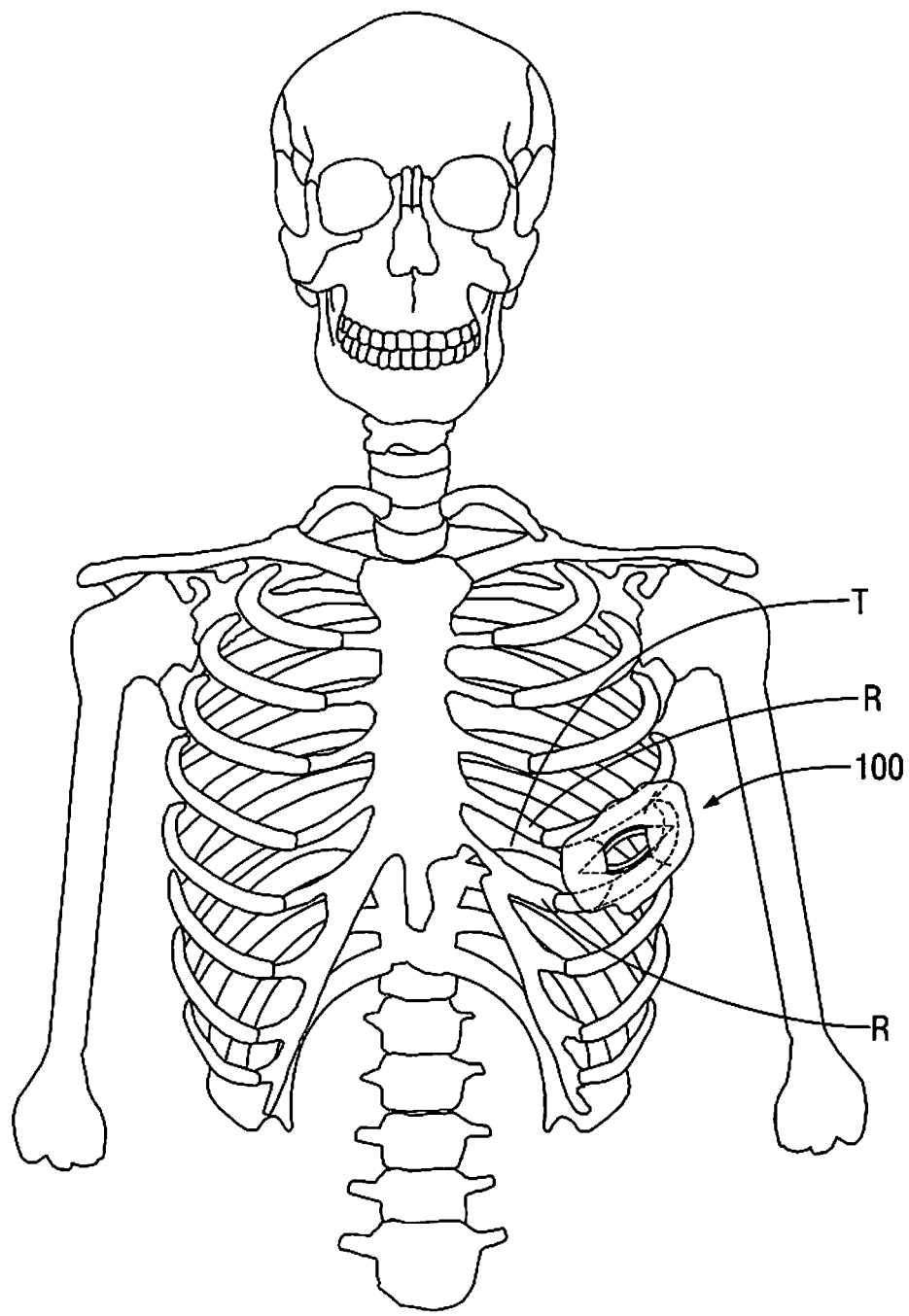
FIG. 1 is a front view illustrating a patient's skeletal structure with a surgical access port in accordance with the present disclosure positioned within the intercostal space defined between adjacent ribs.

Various embodiments of the presently disclosed access assembly, or access port, and methods of using the same, will now be described in detail with reference to the drawings wherein like references numerals identify similar or identical elements. In the drawings, and in the following description, the term "proximal" refers to the end of the access port, or component thereof, that is closer to the clinician and the term "distal" refers to the end that is further from the clinician, as is traditional and conventional in the art. Additionally, use of the term "tissue" should be understood to encompass both the patient's ribs, and any surrounding tissues. It should be also be understood that the term "minimally invasive procedure" is intended to include surgical procedures through small openings/incisions performed within a confined space such as the thoracic cavity.

Referring now to FIGS. 1-7, the presently disclosed surgical access port, generally identified by the reference numeral 100, is depicted as a thoracic port 100 that is configured and dimensioned for insertion into the intercostal space located between the adjacent ribs "R" (FIG. 1) of a patient in order to allow for the insertion and manipulation of one or more surgical instruments within the thoracic cavity. However, it is also envisioned that access port 100 may be configured and dimensioned to provide access to a variety of other internal body cavities and/or tissues. Access port 100 may be formed from any suitable biocompatible material of strength suitable for the purpose described herein, including, but not being limited to, polymeric materials.

Figure 5:
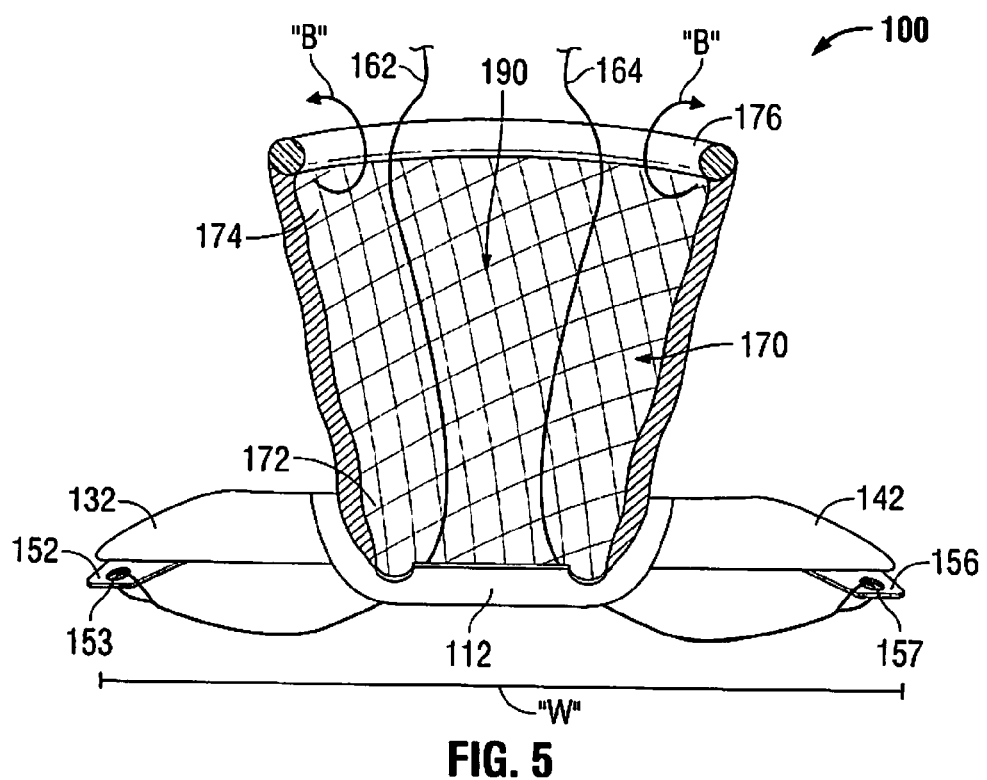
FIG. 5 side view of the access port of FIG. 1 shown in an open position.
Figure 6:
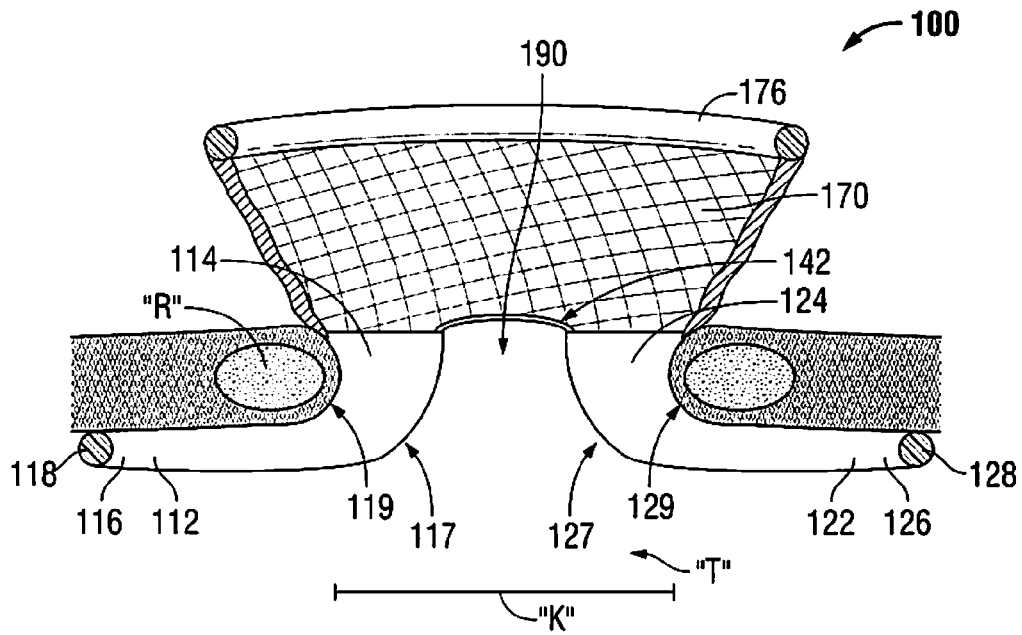
FIG. 6 is a end, cross-sectional view of the access port of FIG. 1 shown in the open position.
Figure 7:
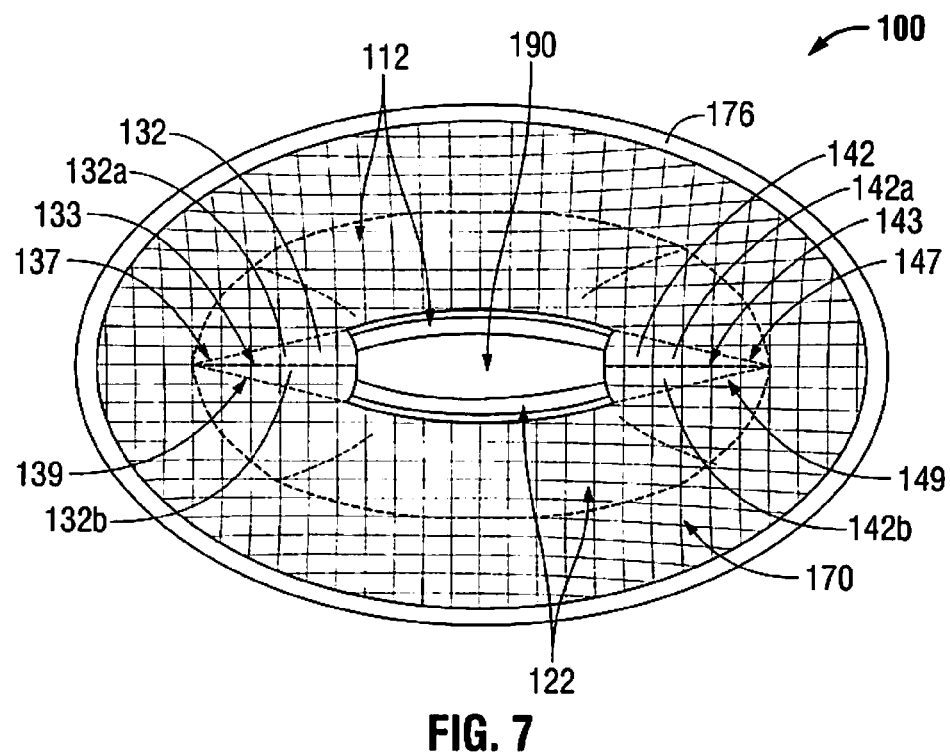
FIG. 7 is a top view of the access port of FIG. 1 shown in the open position.

The access port 100 is configured and dimensioned to extend into a body cavity, e.g., the thoracic cavity "T" (FIG. 1), through the intercostal space, and generally includes a body 110 having first and second side panels 112, 122 and first and second end panels 132, 142. Side panels 112, 122 oppose each other and are interconnected at respective ends thereof by end panels 132, 142. A flexible membrane 170 is coupled to body 110 and extends proximally therefrom. Access port 100 is moveable between a closed, or approximated position (FIGS. 2-4) and an open, or spaced apart position (FIGS. 5-7). More specifically, end panels 132, 142 are moveable between a folded position and an expanded position to move side panels 112, 122 between a concave approximated position and a convex spaced apart position, thus moving access port 100 between the closed position and the open position.

Side panels 112, 122 may be configured to transition between two stable positions, or states: a concave approximated state (FIG. 3) for insertion and removal of access port 100, and a convex spaced apart state (FIG. 6) for creating a passageway 190 through the intercostal space. Side panels 112, 122 define concave inner surfaces 117, 127 when access port 100 is in the closed position, i.e., when side panels 112, 122 are in the concave approximated state, and define convex inner surfaces 117, 127 when access port 100 is in the open position, i.e., when side panels 112, 122 are in the convex spaced apart state. Side panels 112, 122 each may also include a reinforcement strip 118, 128, respectively, disposed therein and positioned toward a respective distal end 116, 126 thereof. Reinforcement strips 118, 128 oppose one another and are configured to facilitate transition of side panels 112, 122 between the concave approximated position and the convex spaced apart position. Reinforcement strips 118, 128 also protect the intercostal nerves when access port 100 is disposed through an opening in tissue by defining the shape of side panels 112, 122 such that side panels 112, 122 are flexed around, and not into, the intercostal nerves. Further, reinforcement strips 118, 128 help maintain access port 100 in the open position, as will be discussed below.

Figure 2:
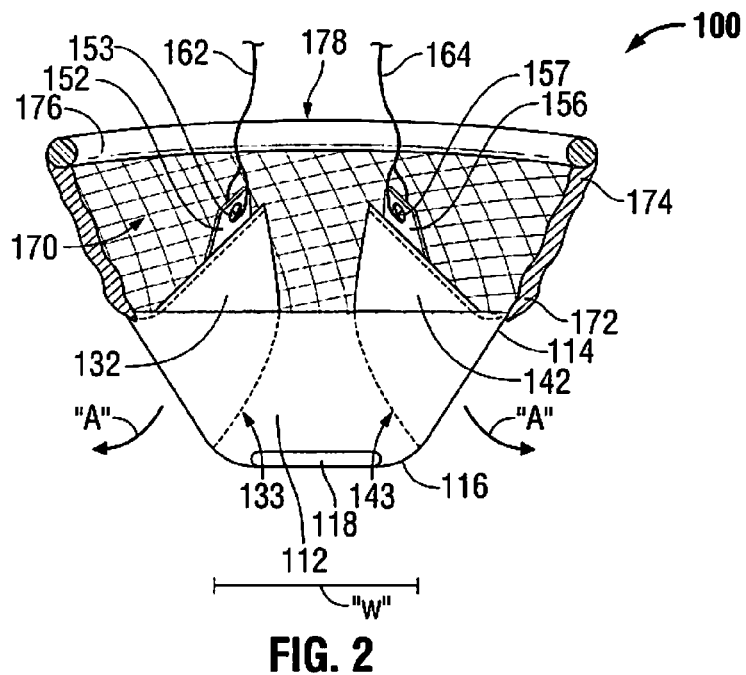
FIG. 2 is a side view of the access port of FIG. 1 shown in a closed position.

As shown in FIG. 2, when access port 100 is in the closed position, side panels 112, 122 are generally quadrilateral in shape, decreasing in width proximally to distally to define a funnel shape configuration. End panels 132, 142 are folded proximally and inwardly between side panels 112, 122 and, as mentioned above, interconnect side panels 112, 122 to one another at opposing ends thereof. Body 110 may be formed as a single piece, i.e., end panels 132, 142, and side panels 112, 122 may be integrally formed as a single body 110. In such embodiments, end panels 132, 142 are hingeable with respect to side panels 112, 122 about fold lines, or living hinges 137, 139, 147, 149 (FIG. 4). Thus, in an unfolded configuration, body 110 may define a continuous circular band of material. However, during manufacturing, fold lines, or living hinges 137, 139, 147, 149 (FIG. 4) are formed within body 110 to define side panels 112, 122 and end panels 132, 142. Additional fold lines, or living hinges 133, 143 are formed within each end panel 132, 142 to divide the respective end panels 132, 142 into end panel sections 132a, 132b and 142a, 142b, respectively. End panels sections 132a, 132b are hingeable with respect to each other about living hinge 133. Similarly, end panel sections 142a, 142b are hingeable with respect to each other about living hinge 143.

As mentioned above, end panels 132, 142 of body 110 of access port 100 are moveable with respect to each other and with respect to side panels 112, 122 between a folded position (FIGS. 2-4) and an expanded position (FIGS. 5-7). As end panels 132, 142 are moved from the folded position to the expanded position, side panels 112, 122 are moved from the concave approximated position to the convex spaced apart position, and thus, access port 100 is moved from the closed position to the open position.

Each end panel section 132a, 142a, 132b, 142b includes a respective tab 152, 156 (tabs of end panels sections 132b and 142b are not shown) having an aperture 153, 157, respectively, defined therein. Tabs 152, 156 are positioned on a proximal end of end panel sections 132a, 142a, respectively. Corresponding tabs (not shown) of end panel sections 132b and 142b are similarly positioned on a proximal end of the respective end panel sections 132b, 142b. More particularly, tab 152 of end panel section 132a is positioned toward living hinge 133 and the tab (not shown) of end panel section 132b is similarly positioned toward living hinge 133 such that the tabs are adjacent one another when end panel 132 is in the folded position. Similarly, with respect to end panel 142, tab 156 of end panel section 142a and the corresponding tab of end panel section 142b are positioned such that the tabs are adjacent one another when end panel 142 is in the folded position. Ribbon, or string 162 is threaded through aperture 153 of tab 152 and though the aperture of the tab (not shown) of end panel section 132b. Similarly, ribbon 164 is threaded through aperture 157 of tab 156 and through the aperture of the tab of end panel 142b. Ribbons 162, 164 are configured to extend proximally through passageway 190 when access port 100 is in the open position such that ribbons 162, 164 may be moved proximally to move end panels 132, 142 from the expanded position to the folded position to move access port 100 from the open position to the closed position. Further proximal movement of ribbons 162, 164 removes access port 100 from the intercostal space.

Flexible membrane 170 is generally funnel shaped, is coupled to proximal ends 114, 124 of side panels 112, 122, respectively, and to end panels 132, 142, and extends proximally therefrom. Distal end 172 of flexible membrane 170 is coupled to side panels 112, 122 and/or end panels 132, 142 to better protect and isolate tissue surrounding access port 100 from the passageway 190 extending therethrough, thus reducing the risk of tissue damage and/or infection during the surgical procedure. It is envisioned that flexible membrane 170 be configured for soft tissue retraction. It is envisioned that it is of sufficient elasticity to permit retraction of a wide range of tissue thicknesses since there may be a wide range of tissue thicknesses among different patients. It is also envisioned that flexible membrane 170 is of sufficient strength to prevent accidental tearing and/or puncture by surgical instrumentation inserted through access port 100. Additionally, it is envisioned that flexible membrane 170 be made from a biocompatible material to reduce the incidents of adverse reaction by a patient upon contact with the patient's tissue. Flexible membrane 170 may also be made of a transparent material to allow the surgeon to better visualize the surgical site and surrounding tissue.

A continuous ring 176 is coupled to a proximal end 174 of flexible membrane 170. Ring 176 may be disposed through a loop 178 formed at the proximal end 174 of flexible membrane 170. Proximal end 174 of flexible membrane 170 may be folded back onto and adhered to flexible membrane 170 to define loop 178 therebetween, or, alternatively, proximal end 174 of flexible membrane 170 may be engaged to ring 178 via any other suitable mechanism. Ring 176 may be made from a flexible or a semi-rigid material. It is envisioned that ring 176 be sufficiently rigid to retain membrane 170 in an open, tensioned configuration, while being somewhat flexible such that ring 176 may be rotated about a circumference thereof to roll, or wind-up flexible membrane 170 therearound, as shown by arrows "B" (FIG. 5). Thus, as ring 176 is rotated in the direction of arrows "B" (FIG. 5), membrane 170 is rolled-up around ring 176 and tensioned, thereby flexing proximal ends 114, 124 of respective side panels 112, 122 further outwardly to retract tissue and/or to expand the passageway 190 extending through access port 100.

Figure 3:
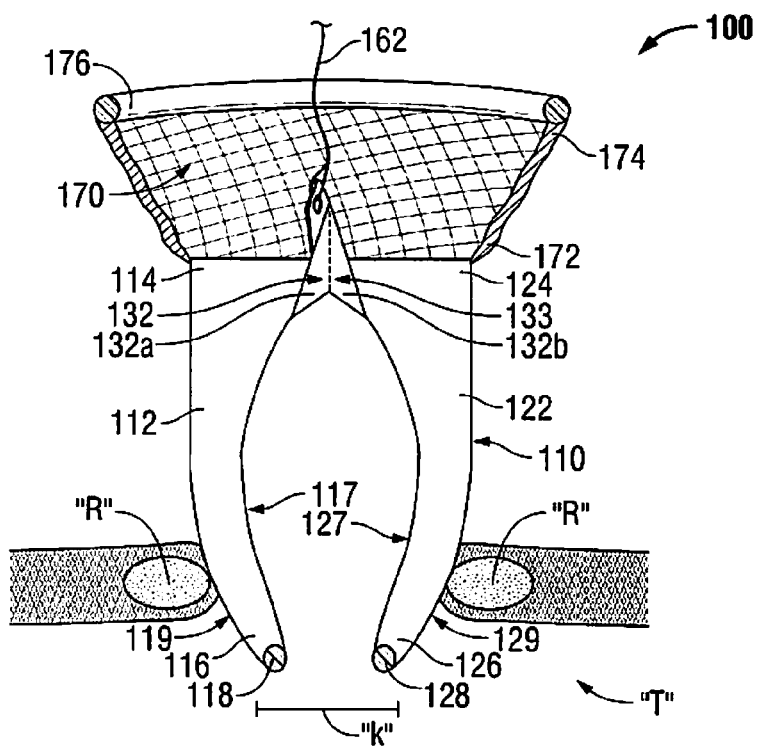
FIG. 3 is an end, cross-sectional view of the access port of FIG. 1 shown in the closed position.
Figure 4:
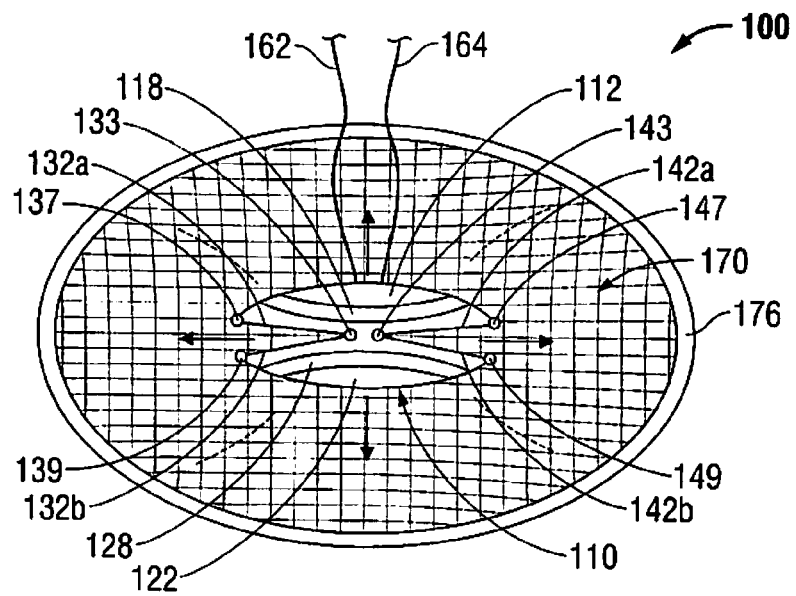
FIG. 4 is a top view of the access port of FIG. 1 shown in the closed position.

FIGS. 2-4 show access port 100 disposed in the closed position with end panel sections 132a and 132b substantially flush, or mating with one another, and positioned between side panels 112, 122 such that living hinge 133 defines an internal angle of about 360 degrees, and such that living hinges 137, 139 define internal angles of about 0 degrees. Similarly, end panel sections 142a, 142b are substantially flush, or mating with one another and are positioned between side panels 112, 122 such that living hinge 143 defines an internal angle of about 360 degrees and such that living hinges 137, 139 define internal angles of about 0 degrees. In other words, in the folded position, end panels 132, 142 are folded internally within access port 100. Additionally, fold lines, or living hinges 137, 139, 147, 149 may be angled proximally with respect to side panels 112, 122 such that end panels 132, 142 are folded proximally (in addition to inwardly) with respect to body 110. As shown in FIG. 2, due to the angled folding of end panels 132, 142, a portion of each end panel 132, 142 extends proximally from between side panels 112, 122. This configuration allows a surgeon to grasp end panels 132, 142 to retain access port 100 in the closed position during insertion and/or removal of access port 100 from an opening in tissue.

As mentioned above, side panels 112, 122 define concave inner surfaces 117, 127 and are positioned adjacent one another in the concave approximated position. Thus, in the closed position, access port 100 defines a minimum width "w" and a minimum thickness "k" to facilitate insertion of access port 100 through relatively small openings in tissue, e.g., a narrow incision in the intercostal space.

End panels 132, 142 of access port 100 may be biased toward the open position. Accordingly, during insertion, the surgeon may grasp access port 100 by end panels 132, 142, as mentioned above, to retain end panels 132, 142 in the folded position against the bias and, thus, to retain access port 100 in the closed position. As will be described in greater detail below, once access port 100 is positioned as desired. e.g., once body 110 of access port 100 is inserted through the intercostal space between two ribs "R," the surgeon may release end panels 132, 142 such that, under the bias, end panels 132, 142 are moved to the expanded position, moving side panels 112, 122 from the concave approximated position to the convex spaced apart position and, thus, moving access port 100 from the closed position to the open position.

In the closed position of access port 100, flexible membrane 170 extends proximally from side panels 112, 122. Flexible membrane 170 defines a funnel shape when access port 100 is in the closed position. More specifically, ring 176 retains proximal end 174 of flexible membrane 170 in an open configuration while distal end 172 of flexible membrane 170 defines a smaller diameter due to the engagement of distal end 172 of flexible membrane 170 with side panels 112, 122, which are approximated with respect to one another in the closed position of access port 100.

FIGS. 5-7 show access port 100 in the open position wherein passageway 190 extends therethrough to provide access into the thoracic cavity "T." In the open position, end panels 132, 142 have rotated, or moved distally and outwardly to the expanded position and side panels 112, 122 are flexed outwardly to define convex inner surfaces 117, 127, respectively, and, correspondingly, concave outer saddles 119, 129, respectively, as best shown in FIG. 6. Concave outer saddles 119, 129 are configured to seat a rib "R" of a patient therein to protect the rib "R," the intercostal nerve, and surrounding tissue. Additional cushioning (not explicitly shown) may line saddles 119, 129 to provide further protection to ribs "R" and to surrounding tissue. With reference to FIG. 6 in particular, distal ends 116, 126 of side panels 112, 122, respectively, extend outwardly from the opening in tissue below the ribs "R," i.e., within the thoracic cavity "T," while proximal ends 114, 124 of side panels 112, 122, respectively, extend proximally through the incision in the intercostal space to expand the adjacent tissue and/or ribs "R" and to define passageway 190 therebetween. In other words, body 110 of access port 100, in the open position, generally defines an upside down tulip, or inverted funnel-shaped configuration wherein passageway 190 extends through the intercostal space defined by the proximal portion of body 110 of access port 100, and wherein the distal portion of body 110 of access port 100 extends radially outwardly from passageway 190 within the thoracic cavity "T." In this open position, access port 100 defines a maximum width "W" and a maximum thickness "K." More specifically, the outward flexion of side panels 112, 122 expands the intercostal space, thus maximizing passageway 190, defining the maximum thickness "K." The expansion of end panels 132, 142 outwardly gives access port 100 the maximum width "W."

In the open position, flexible membrane 170 extends proximally from side panels 112, 122 and remains substantially proximal (external) of the opening in tissue. As can be appreciated, flexible membrane 170 defines a funnel shape in the open position, since the diameter of ring 176, which retains flexible membrane 170 in the open position at a proximal end 174 thereof is greater than the diameter of passageway 190 defined by side panels 112, 122 which are engaged to distal end 172 of flexible membrane 170. Flexible membrane 170 may be tensioned, e.g., by rolling flexible membrane 170 about ring 176 such that membrane 170 is disposed about an external surface of tissue. Tensioning flexible membrane maintains side panels 112, 122, and thus tissue, e.g., ribs "R," in an expanded position. Thus, in the open position, passageway 190, lined by proximal ends 114, 124 of side panels 112, 122, respectively, extends through the intercostal space; membrane 170 extends outwardly along the external surface of tissue; and distal ends 116, 126 of side panels 112, 122, respectively, extend laterally outwardly along an internal surface of tissue. Reinforcement strips 118, 128 retain side panels 112, 122 saddled about ribs "R" and, thus, help maintain the position of access port 100 within the intercostal space.

As can be appreciated, and as mentioned above, when access port 100 is in the open position, body 110 forms an inverted funnel shape and flexible membrane 170 forms a funnel shape such that access port 100 generally defines an hourglass configuration. The passageway 190 through the intercostal space forms the central portion of the hourglass configuration, the externally disposed flexible membrane 170 extending radially outwardly from passageway 190 forms the proximal portion of the hourglass configuration and the internally disposed side panels 112, 122 and end panels 132, 142 extending radially outwardly from passageway 190 define the distal portion of the hourglass configuration.

The use and operation of the access port 100 will be now discussed during the course of a minimally invasive thoracic procedure by way of example and with reference to FIGS. 1-7. As will be appreciated, access port 100 is easily inserted, manipulated, and removed from a patient's body. Further, the access port 100 is minimally intrusive, flexible to conform to a patient's anatomy, and provides good visibility into the thoracic cavity "T" (FIG. 3). Additionally, the low-profile configuration of access port 100 is particularly advantageous, for example, in the removal, or retrieval, of tissue specimens from within the body.

Initially, an opening, or incision, is made in the patient's outer tissue wall of the thoracic body cavity by conventional means. The incision is made between adjacent ribs "R" (FIG. 1), extending along the intercostal space, and is relatively narrow and elongated (FIG. 1).

In preparation for insertion through the incision, access port 100 is moved to the closed position wherein, as mentioned above, side panels 112, 122 are in the concave approximated position and wherein end panels 132, 142 are folded between side panels 112, 122, such that access port 100 defines a minimum width "w" and minimum thickness "k." It is envisioned that the minimum width "w" and minimum thickness "k" be sufficiently small to allow access port 100 to be inserted at least partially through the incision. Accordingly, access port 100 may be configured to define different minimum widths and thicknesses, depending on the anatomy of the patient and/or the specific procedure to be performed.

Referring now to FIG. 2, with access port 100 positioned as shown and as described above, a surgeon may grasp end panels 132, 142 and translate access port 100 distally through the incision. Grasping end panels 132, 142 inhibits end panels 132, 142 from moving toward the biased, expanded position, and, thus, retains access port 100 in the closed position.

As best shown in FIG. 3, access port 100 is translated distally through the incision in tissue until body 110 of access port 100 is disposed through the incision and such that flexible membrane 170 extends proximally from the incision. Ribbons 162, 164 extend from end panels 132, 142 proximally through the incision.

FIG. 4 shows the position of access port 100 once inserted within the intercostal space but prior to deployment of access port 100 into the open position. As shown, side panels 112, 122 are concave and approximated with respect to one another, and end panels 132, 142 are folded inwardly and proximally with respect to side panels 112, 122. In the position shown in FIG. 4, access port 100 has been inserted into the intercostal space however, since body 110 remains in the closed position, ribs and/or surrounding tissue are undisturbed, or unexpanded. Thus, at this point, access port 100 may be maneuvered into the desired position without substantially disturbing surrounding tissue.

With access port 100 in position as described above, body 110 of access port 100 may be released (or moved) to the open position to define an access passage 190 through the intercostal space. To expand access port 100, the surgeon releases end panels 132, 142, allowing end panels 132, 142 to move, under the bias of end panels 132, 142, from the folded position toward the expanded position. End panels 132, 142 are angled, or hinged, outwardly and distally in the direction of arrows "A" (FIG. 2) to achieve the expanded position. As end panels 132, 142 are angled outwardly and distally, side panels 112, 122 are flexed outwardly and urged apart from one another to define passageway 190 therethrough. Upon further expansion of end panels 132, 142, side panels 112, 122 reach a critical point wherein side panels 112, 122 "pop" from the concave state (FIG. 3) to the convex state (FIG. 6) and their distal ends 116, 126 are urged, or flexed further apart to surround ribs "R" for seating ribs "R" within saddles 119, 129. The outward expansion and flexion of side panels 112, 122 also acts to separate (retract) tissue adjacent ribs "R," thereby expanding the intercostal space.

Upon transition from the concave approximated state to the convex spaced apart state, side panels 112, 122 release outwardly to the spaced apart position (the convex, spaced apart stable state). In other words, due to the bistable configuration of side panels 112, 122, side panels 112, 122 are biased toward the spaced apart position once side panels 112, 122 are transitioned to the convex state. Similarly, once side panels 112, 122 are transitioned back to the concave state for removal, side panels 112, 122 become biased toward the approximated position.

As end panels 132, 142 are angled distally and outwardly, the internal angle defined by living hinges 133 and 143 decreases. In other words, as end panels 132, 142 are moved distally and outwardly, end panel sections 132a-b and 142a-b are angled apart from each other about living hinges 133, 143, respectively. Similarly, end panel sections 132a-b, 142a-b are angled with respect to side panels 112, 122 such that the internal angles defined by living hinges 137, 139, 147, 149 are increased. As can be appreciated, moving end panel sections 132a-b and 142a-b apart from one another and angling end panel sections 132a-b, 142a-b with respect to side panels 112, 122 urges side panels 112, 122 outwardly, as mentioned above.

FIGS. 5-7 shows access port 100 disposed in the open position. As shown in FIG. 5, end panels 132, 142 have been expanded distally and outwardly to the expanded position. Similarly, as shown in FIG. 6, side panels 112, 122 have been flexed and expanded distally and outwardly to the spaced apart position. Thus, the up-side down tulip, or inverted funnel shape is achieved, wherein the proximal portion of body 110 expands the intercostal space to define passageway 190 therethrough and wherein the side panels 112, 122 and end panels 132, 142 are expanded outwardly within the thoracic cavity "T" to retain body 110 of access port 100 in the expanded position, and to protect ribs and surrounding tissue.

With continued reference to FIGS. 5-7, flexible membrane 170 extends proximally from the incision and is retained in an open configuration by ring 176. As mentioned above, ring 176 may be rotated about its circumference, in the direction of arrows "B," to selectively tension flexible membrane 170. That is, as ring 176 is rolled, the flexible membrane 170 is rolled therearound and increasingly tensioned. More particularly, flexible membrane 170 is tensioned radially outwardly from the incision in tissue (toward ring 176) such that flexible membrane 170 helps maintain (or further expand) side panels 112, 122 in the spaced apart position, retracting tissue adjacent ribs "R." Further, with membrane 170 extending proximally and radially outward from the incision along the external surface of tissue and with side panels 112, 122 extending distally and radially outward from the incision along the internal surface of tissue (the hourglass configuration), tissue surrounding the incision is protected from contamination, tearing and/or puncture.

With access port 100 retained in the open position, surgical instrumentation may be inserted through passageway 190 to perform the surgical procedure within the body cavity. As shown in FIG. 6, side panels 112, 122 maintain passageway 190 while protecting the incision and surrounding tissue. Ribs "R" are protected within saddles 119, 129 by side panels 112, 122. Flexible membrane 170 protects the external surface of tissue. Additionally, the low-profile configuration of access port 100, when ring 176 is rolled to tension flexible membrane 170 along the external surface of tissue, allows for greater access to the thoracic cavity "T" and for greater manipulation of instrumentation disposed through passageway 190.

The inwardly facing surfaces 117, 127 of side panels 112, 122, respectively, may be coated with a lubricant, or gel, to aid in the insertion and removal of surgical instrumentation and/or tissue specimen from access port 100.

Upon completion of the surgical procedure, ring 176 may be unrolled, to untension flexible membrane 170. Next, the surgeon may grasp ribbons 162, 164, which extend proximally from the incision, and may translate ribbons 162, 164 proximally. As ribbons 162, 164 are pulled proximally, end panels 132, 142 are moved inwardly and proximally from the expanded position of FIG. 5 to the folded position of FIG. 2. Moving end panels 132, 142 from the expanded position to the folded position moves side panels 112, 122 from the spaced apart position back toward the approximated position. When side panels 112, 122 reach the critical point, side panels 112, 122 "pop" back from the spaced apart convex state to the approximated concave state, allowing side panels 112, 122 to more easily move back to the approximated position. Thus, translating ribbons 162, 164 proximally moves access port from the open position to the closed position. Further proximal translation of ribbons 162, 164 translates body 110 of access port 100 proximally, removing access port 100 from the incision in tissue. Alternatively, with access port 100 in the closed position, the surgeon may grasp end panels 132, 142 to translate access port 100 proximally from the incision. Finally, the incision may be closed off, e.g., sutured closed.

Figure 8:
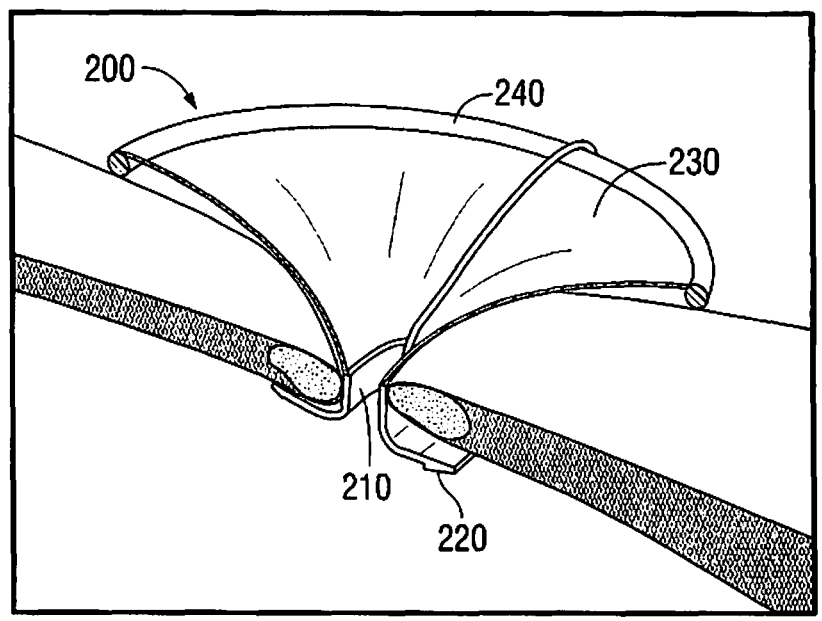
FIG. 8 is a cross-sectional view of an alternate embodiment of an access port of the present disclosure.
Figure 9:
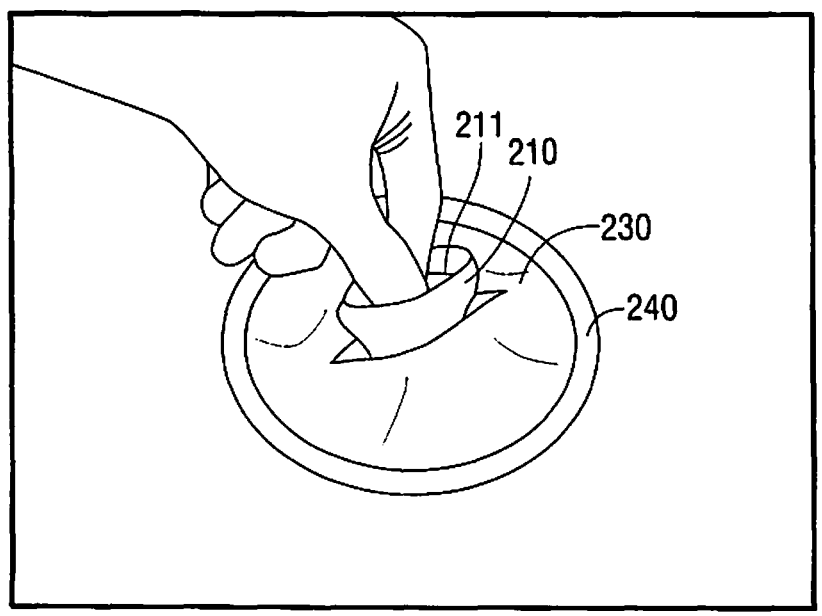
FIGS. 9-14 are perspective views showing the method of insertion of the access port of FIG. 8.
Figure 10:
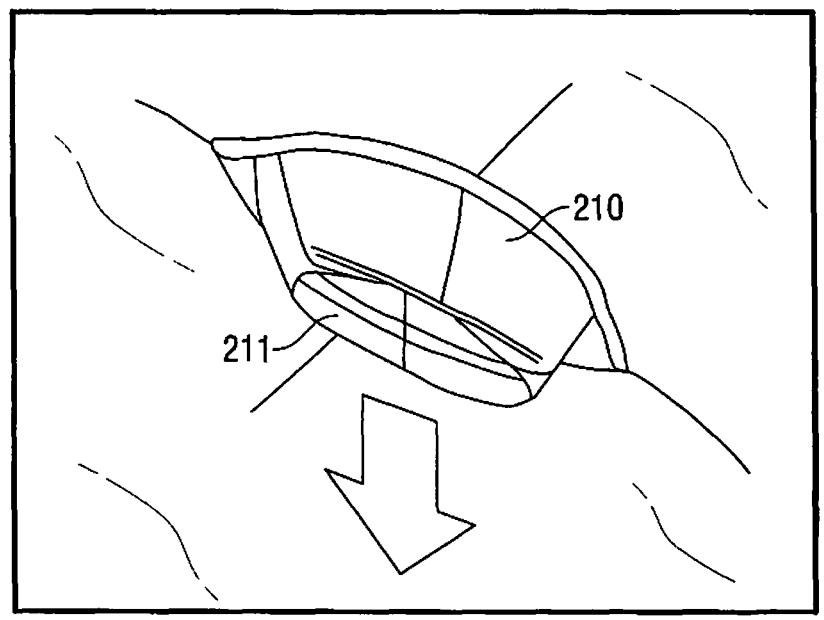

FIGS. 8-18, illustrate an alternate embodiment of the access port. Access port 200 has a rigid support 210, preferably substantially oval in cross section, and a plurality of flexible panels or petals 220 extending from the support 210. The petals 220 are movable from a first position where they are constrained within the support 210 for delivery, to a placement position, where the petals 220 extend into the incision and radially from the support 210 to contact the tissue adjacent the incision as shown in FIG. 8.

Extending from the opposing side of the support 210 is an elastic membrane 230. Membrane 230 is attached at one end to a circumferential portion of the support 210 and at the other end to a substantially circular ring 240, thus extending in a 360 degree area adjacent the incision. The circular ring 240 is movable to adjust the tension on the elastic membrane 230. In one embodiment, rolling of the ring 240 applies tension to the elastic membrane 230 to retract soft tissue adjacent the incision in a manner similar to the access port 100 of FIGS. 1-7. In an alternate embodiment, the ring can have two or more separable components which include a ratchet to allow for adjustability of the diameter of the ring to tension the membrane 230. Other ways to adjust the ring to tension the membrane are also contemplated.

Figure 11:
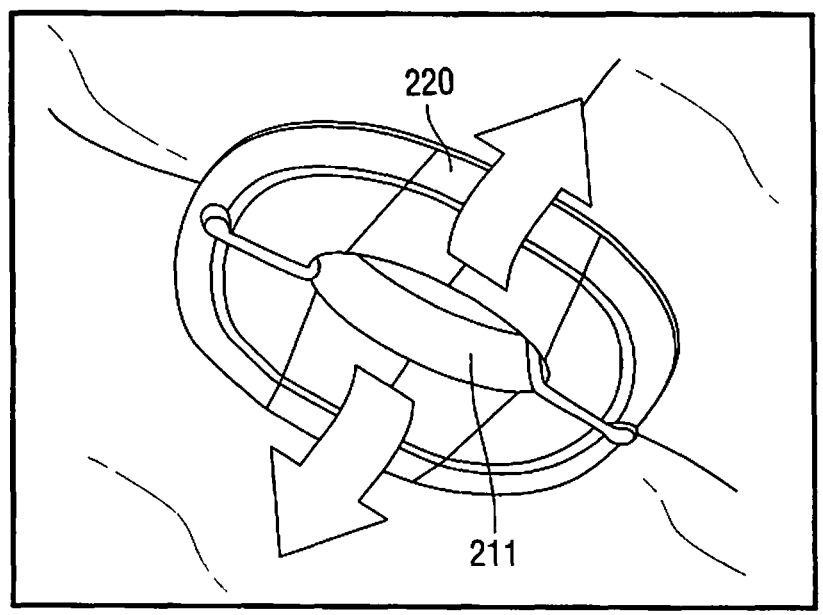
Figure 12:
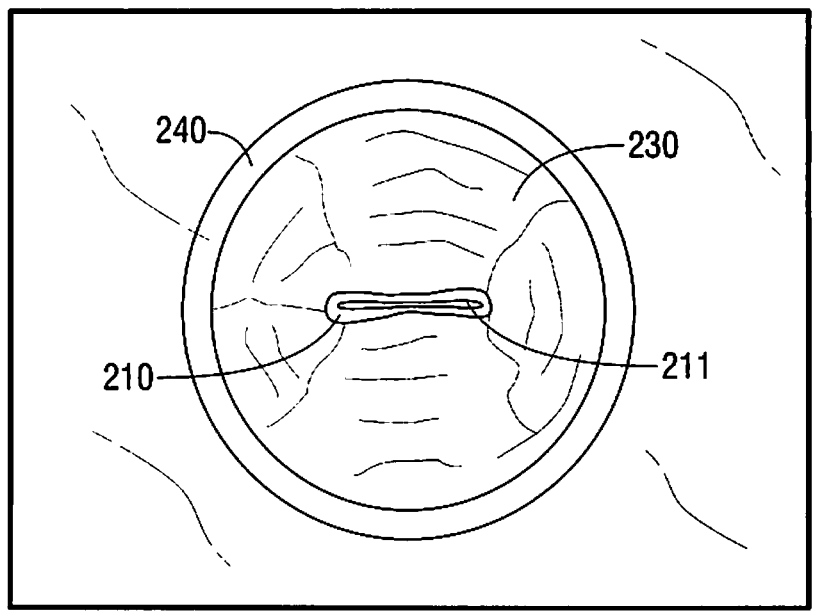
Figure 13:
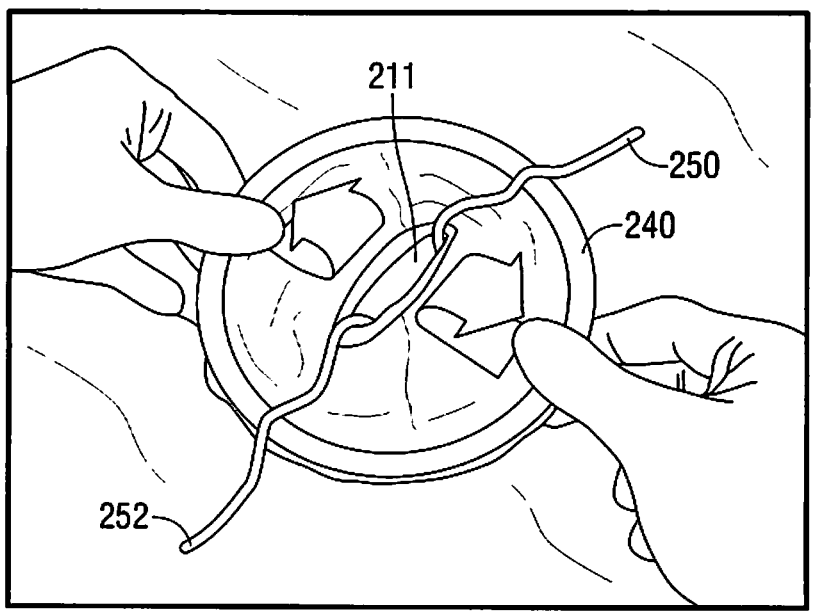
Figure 14:
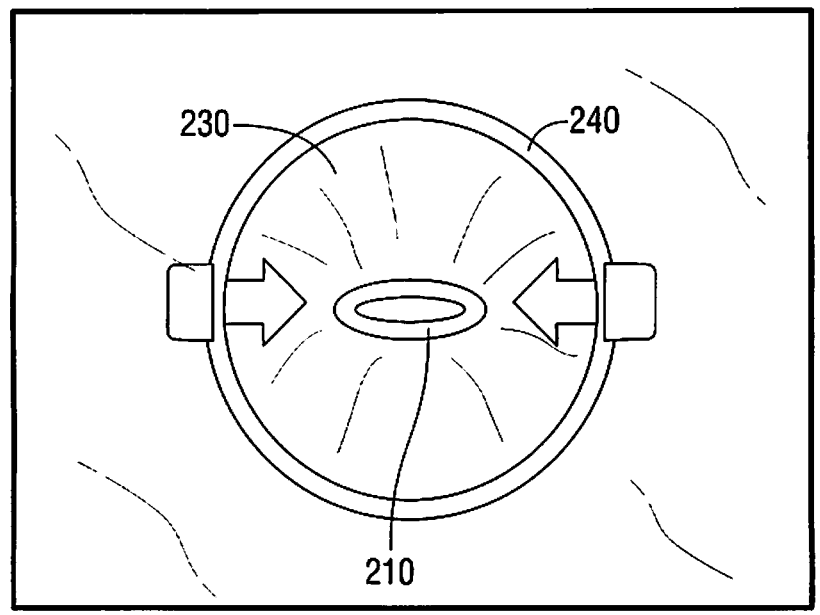

Referring to FIGS. 9-12, the insertion of access port 200 will now be described. Initially, rigid support 210 is inserted through the incision (FIGS. 9 and 10) with the petals 220 in the collapsed delivery position within the support 210. As seated within the incision, a proximal portion of the rigid support 210 preferably extends slightly external of the incision. Next the surgeon inserts his finger through the opening 211 in the support 210 to push the petals 220 out of the support 210 and into the body cavity where they move to their natural spread position as shown in FIG. 11. The petals 220 in some embodiments can be configured to have a spaced apart (spread) stable state such that pushing of the petals 220 beyond a certain state causes them to "pop" to the spaced position. Thus, the petals can be bistable i.e. retainable in both the collapsed and delivery positions. Subsequently, the outer ring 240 is rolled as shown by the arrows in FIGS. 13 and 14 so the elastic membrane 230 is tensioned, thereby retracting (spreading) the soft tissue at the edges of the incision. The port 200 then allows for insertion of instrumentation therethrough to access the body cavity.

Figure 15:
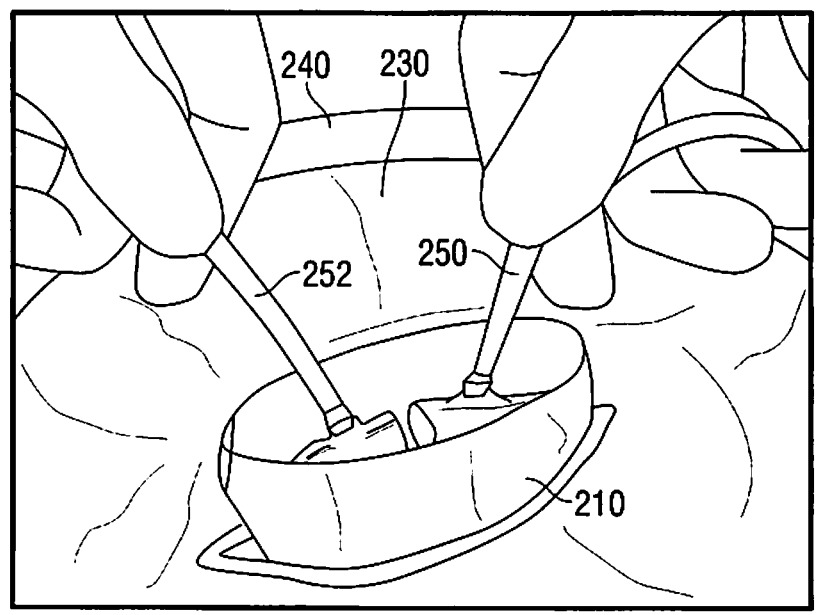
FIGS. 15-18 are perspective views showing the method of removal of the access port of FIG. 8.
Figure 16:
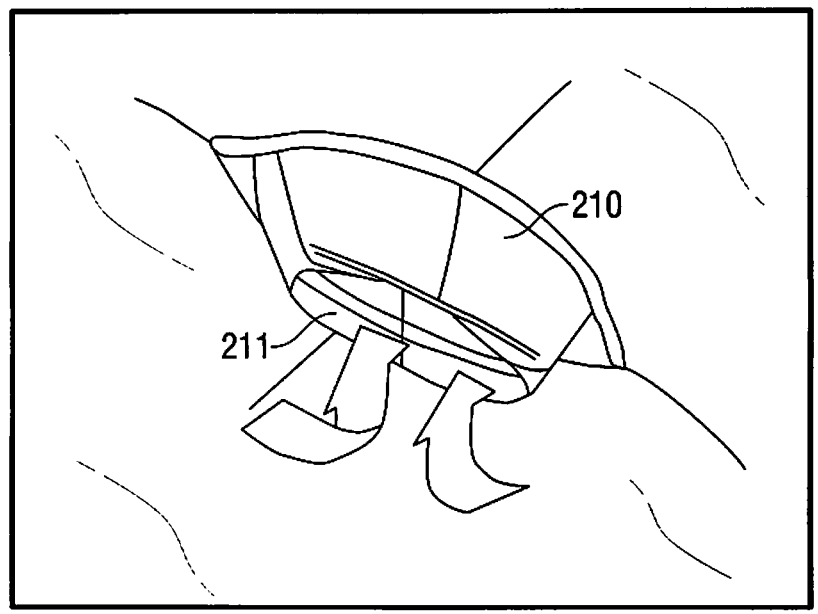
Figure 17:
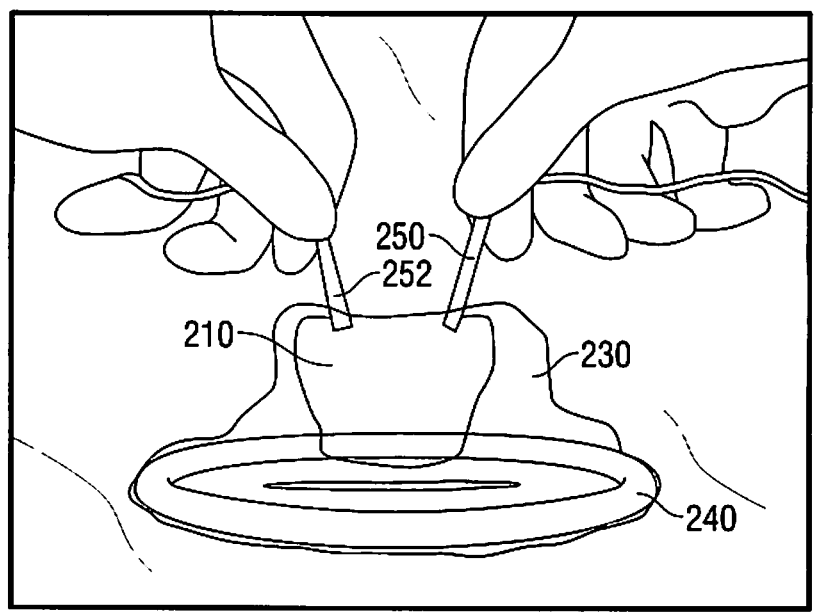
Figure 18:
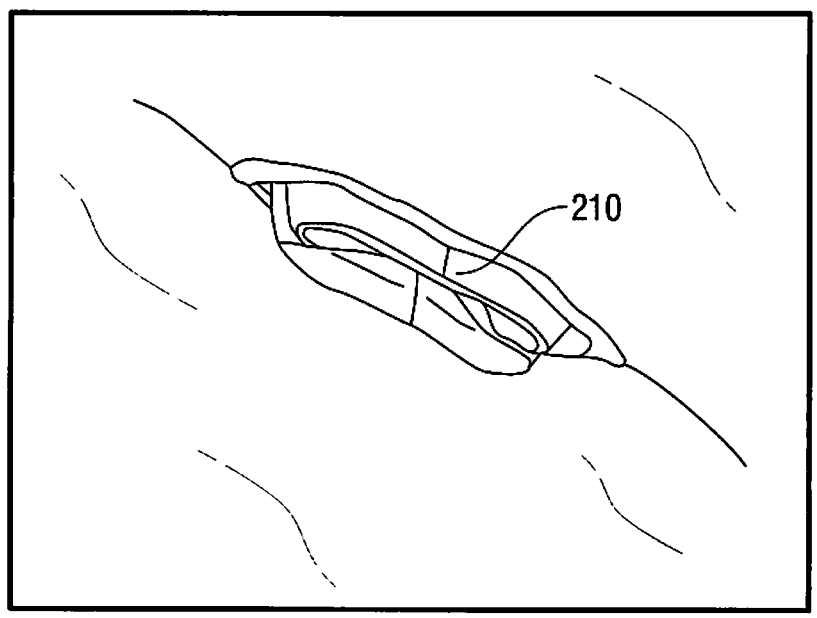

To remove the access port 200, outer ring is unrolled, at least partially, to untension membrane 230, and then ribbons 250, 252, preferably attached to the rigid petals 220, are pulled upwardly as shown in FIGS. 15 and 16, thus retracting the petals 220 into the support 210 to allow for removal of the port in the direction of the arrow of FIG. 18. Further pulling of the ribbons 250, 252 removes the rigid support 210 from the incision to remove the access port 200, or the rigid support 210 can be grasped and pulled from the incision to remove the access port 200.

Although described for use in thoracic procedures, it should also be understood that the access ports described herein can be used in other minimally invasive surgical procedures.

Persons skilled in the art will understand that the devices and methods specifically described herein and illustrated in the accompanying figures are non-limiting exemplary embodiments, and that the description, disclosure, and figures should be construed merely exemplary of particular embodiments. It is to be understood, therefore, that the present disclosure is not limited to the precise embodiments described, and that various other changes and modifications may be effected by one skilled in the art without departing from the scope or spirit of the disclosure. Additionally, it is envisioned that the elements and features illustrated or described in connection with one exemplary embodiment may be combined with the elements and features of another without departing from the scope of the present disclosure, and that such modifications and variations are also intended to be included within the scope of the present disclosure. Accordingly, the subject matter of the present disclosure is not to be limited by what has been particularly shown and described, except as indicated by the appended claims.

What is claimed is:

1. A surgical access assembly for positioning within an opening in tissue, the surgical access assembly comprising:
    a body composed of substantially rigid material and having an opening dimensioned and configured to receive surgical instruments therethrough;
    a plurality of flexible members coupled to the body, the plurality of flexible members movable between a collapsed position, wherein the plurality of flexible members are constrained within the body, and an expanded position, wherein the plurality of flexible members extend distally from the body;
    an elastic membrane coupled to the body at a first end thereof and extending proximally from the body; and
    an outer tensioning member connected to a second, opposite end of the elastic membrane, the tensioning member movable to tension the elastic membrane to retract soft tissue adjacent the opening in tissue.

2. The access assembly according to claim 1, wherein the tensioning member comprises a ring, the ring configured to rotate about a circumference thereof to roll the membrane therearound for selectively tensioning the membrane.

3. The access assembly according to claim 1, wherein the access assembly further comprises at least one ribbon for retracting the flexible members from the expanded position back to the collapsed position for removal.

4. The access assembly according to claim 1, wherein the flexible members are biased toward the expanded position.

5. The access assembly according to claim 1, wherein the flexible membrane defines a funnel shaped configuration.

6. The access assembly according to claim 1, wherein the body is substantially oval.

7. The access assembly according to claim 1, wherein the flexible members are stable in the collapsed position.

8. The access assembly according to claim 1, wherein the flexible members are stable in the expanded position.

9. The access assembly according to claim 1, wherein the flexible members are bistable.

* * * * *